United States Patent [19]

Olovson et al.

[11] Patent Number: 5,731,002
[45] Date of Patent: Mar. 24, 1998

[54] VETERINARY COMPOSITION

[75] Inventors: Stig-Göran Arthur Olovson, Ljungskille; Åke Gunnar Pilbrant, Kungsbacka, both of Sweden

[73] Assignee: Astra Aktiebolag, Sodertalje, Sweden

[21] Appl. No.: 235,258

[22] Filed: Apr. 29, 1994

[30] Foreign Application Priority Data

Apr. 30, 1993 [SE] Sweden .................. 9301489

[51] Int. Cl.$^6$ .................. A61K 9/16
[52] U.S. Cl. .................. 424/484; 424/464; 424/471; 424/472; 424/4; 424/480; 424/482; 424/489; 514/338; 514/360
[58] Field of Search .................. 424/480–482, 424/475, 471, 472, 464, 484, 489, 490; 514/338, 360

[56] References Cited

U.S. PATENT DOCUMENTS

| | | | |
|---|---|---|---|
| 3,336,192 | 8/1967 | Sarett | 514/338 |
| 3,746,490 | 7/1973 | Marsland et al. | 424/219 |
| 4,786,505 | 11/1988 | Lovgren et al. | 424/468 |
| 5,215,974 | 6/1993 | Alminger et al. | 514/80 |

FOREIGN PATENT DOCUMENTS

| | | |
|---|---|---|
| 277741 | 8/1988 | European Pat. Off. . |
| 496437 | 7/1992 | European Pat. Off. . |
| 519365 | 12/1992 | European Pat. Off. . |
| 8806893 | 9/1988 | WIPO . |

OTHER PUBLICATIONS

Karcher et al J. Vet. Int. Med. vol. 4 (5) pp. 247–253 1990.
Borgsteede: Tijdschrift VoorDiergeneeg runde vol. 110 (6) pp. 237–238, 1985.
Fed. Regist. 58(98) p. 29777 May 24, 1993.
Fed. Regist: Oct. 29, 1976 p. 47424.
FDA–FDC Reports vol. 45 #34 pp. 8–10 Aug. 22, 1983.
FDA–FDC Reports vol. 39 #25 p. TYG–9 Jun. 20, 1977.
Polish Specification No P–264817 and English translation (abstract).

*Primary Examiner*—Neil S. Levy
*Attorney, Agent, or Firm*—White & Case

[57] ABSTRACT

A stable, oral pharmaceutical composition comprising a proton pump inhibitor and a gelling agent designed for the treatment of gastric acid related diseases in animals, the process for preparation of the composition and the use thereof.

17 Claims, No Drawings

5,731,002

VETERINARY COMPOSITION

TECHNICAL FIELD

The invention relates to an oral pharmaceutical composition comprising a proton pump inhibitor (PPI) and is designed for the treatment of gastric acid related diseases in animals.

BACKGROUND OF THE INVENTION

Proton pump inhibitors are potent inhibitors of gastric acid secretion and are used for the treatment of gastric acid related diseases in humans, such as for instance gastric and duodenal ulcers. These substances are susceptible to degradation/transformation in acid reacting and neutral media. Pharmaceutical formulations for oral administration to humans are preferably enteric-coated. These formulations are sensitive to moisture and must be stored in well-closed, tight containers during long-term storage.

Peptic ulcer diseases are common also in some animals, especially in horses and camels. Other animals of interest for treatment of peptic ulcer diseases are for example dolphins, sea-lions, llamas, dogs, cats and pigs. By gastro-endoscopic evaluation of horses, ulcers have been found in the squamous mucosa, the non glandular fundus, the glandular stomach and the duodenum. The aetiology of gastroduodenal ulcers in the equine species is mainly unknown but stress appears to play an important role in some cases.

Anti-ulcer compounds such as for instance histamine-2-receptor antagonists have reportedly been administered several times a day to horses by oral or naso-gastric tubes. This procedure can be traumatic and may require light sedation of the horse. Trained persons are required for the administration.

Omeprazole and other proton pump inhibitors are potent inhibitors of gastric acid secretion in animals. They block the production of gastric acid by inhibition of H⁺K⁺-ATPase, the enzyme responsible for the production of hydrogen ions in the parietal cells. The proton pump inhibitors cause profound acid suppression and unlike most other anti-ulcer compounds such as for instance the $H_2$-blockers, omeprazole can be given once daily. According to the present invention enteric-coated beads containing omeprazole in a gel formulation can easily be applied onto the dorsal part of the tongue of the horse during field conditions and is well accepted by the horses.

Such a moist gel comprising enteric-coated beads of proton pump inhibitors is not stable during long-term storage at room temperature and must be prepared ex tempore. Today there exists no such formulation on the market.

Omeprazole, 5-methoxy-2(((4-methoxy-3,5-dimethyl-2-pyridinyl)methyl)sulfinyl)-1H-benzimidazole, is disclosed in European patent no 5129 as a potent inhibitor of gastric acid secretion.

Lansoprazole, 2-[[[3-methyl-4-(2,2,2-trifluoroethoxy)-2-pyridyl]methyl]sulfinyl]-1H-benzimidazole, is disclosed in European patent no 174 726 as a potent inhibitor of gastric acid secretion.

Pantoprazole is disclosed in European patent no 166 287 as a potent inhibitor of gastric acid secretion.

Leminoprazole is disclosed in UK patent no 2 163 747.

SUMMARY OF THE INVENTION

The object of the present invention is to provide oral pharmaceutical compositions for easy administration to horses and other animals. The proton pump inhibitor is in the form of dry particles, such as beads or tablets, which are coated with one or more coatings one of which is an enteric-coating. The beads or tablets can be prepared by compaction, crystallisation, applying a solution or suspension of the proton pump inhibitor onto inert cores, extrusion and spheronisation or similar processes. The enteric-coated beads or tablets are mixed with dry gelling agent(s), such as for instance xanthan gum, guar gum, locust bean gum, tragacanth, modified cellulose derivatives or similar gel forming compounds. When water is added to this mixture a paste-like gel is formed (having the consistency of a paste). The gel is for example applied dorsally at the tongue of the animal such as a horse with a suitable applicator.

DETAILED DESCRIPTION OF THE INVENTION

Proton pump inhibitors used in the compositions of the invention are compounds of the general formula I

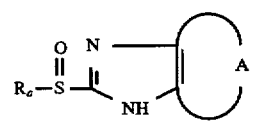

wherein $R_a$ is

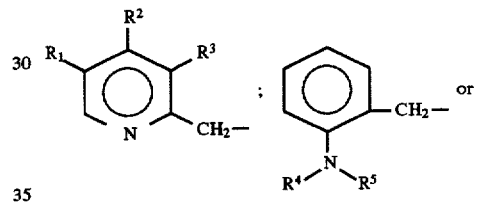

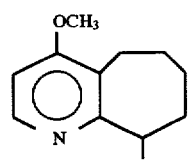

$R^1$ and $R^3$ are independently selected from hydrogen, lower alkyl, lower alkoxy and halogen, $R^2$ is selected from hydrogen, lower alkyl, lower alkoxy, lower alkoxy—lower alkoxy, lower fluoralkoxy and

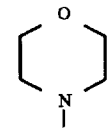

$R^4$ and $R^5$ are independently selected from lower alkyl. A is

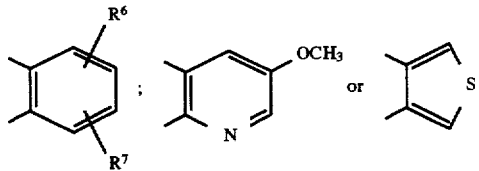

$R^6$ and $R^7$ are independently selected from hydrogen, lower alkyl, lower alkoxy, lower fluoroalkoxy, lower fluoroalkyl, halogen.

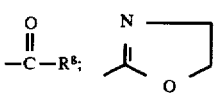

wherein R⁸ is lower alkyl or lower alkoxy.

Lower alkyl in the present invention means an alkyl group having 1–5 carbon atoms.

Lower alkoxy in the present invention means an alkoxy group having 1–5 carbon atoms.

Examples of proton pump inhibitors according to formula I are

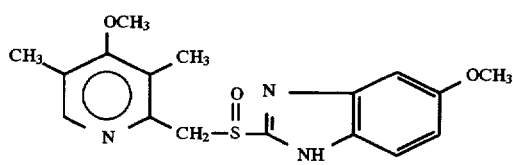

Omeprazole

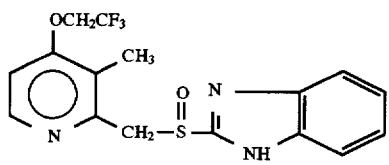

Lanzoprazole

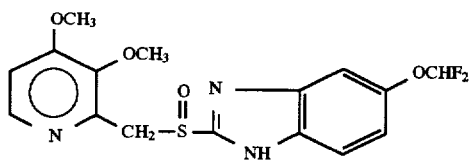

Pantoprazole

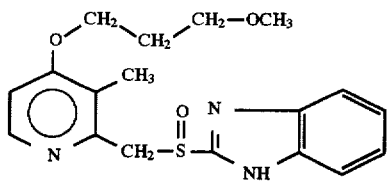

E-3810

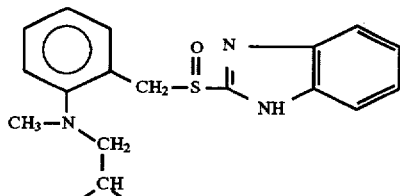

Leminoprazole

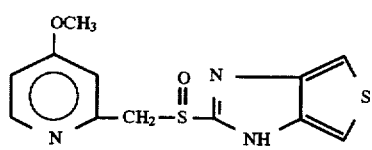

S-4216

The proton pump inhibitors used in the compositions of the invention may be used in neutral form or in the form of a basic salt, such as for instance the $Mg^{2+}$, $Ca^{2+}$, $Na^+$, or $K^+$ salts, preferably the $Mg^{2+}$ of $Na^+$ salts. Further where applicable, a compound listed above may be used in racemic form or in the form of a substantially pure enantiomer.

In one embodiment of the invention the enteric-coated particles are mixed with suitable substances, such as for instance suitable inorganic or organic water soluble salts of potassium, calcium, magnesium or aluminium. When a water solution of a suitable polymeric compound or compounds, such as for instance kappa-carrageenan, pectin, anionic polymers known to give gels with positively charged metal ions, or similar compounds, is added to the mixture a paste-like gel is formed through the interaction of the ions with the polymers.

In another embodiment of the invention the enteric-coated particles are mixed with suitable constituents. When a low-viscous solution of a temperature-sensitive polymer, such as for instance ethylhydroxyethylcellulose (EHEC) or polyethylenepolypropylene glycols or similar substances, is added and the system is warmed to temperatures of 33°–35° C. or higher a viscous paste-like gel is formed.

In still another embodiment of the invention the enteric-coated particles are mixed with suitable substances in the form of gelforming agents, such as dry gelling agent. As gelforming agents can be used for example acacia, agar, alginic acid, sodium carboxymethyl cellulose, hydroxypropyl cellulose, hydroxypropyl methylcellulose or other similar cellulose derivatives, fucoidan, xanthan gum, furcellaran, laminaran or similar gelforming agents.

In a preferred embodiment of the invention the proton pump inhibitor is omeprazole.

The amount of the different components of the composition can vary and will depend on various factors such as for example the individual requirement of the animal treated.

The amount of gelforming agent can vary but is within the range 0.02–20% by weight calculated on the amount of wet gel, preferably in the range of 0.2–20% and especially 0.5–5% by weight.

The amount of active substance, i.e. the enteric-coated particles, depends on the individual dosages for the animal. For example the amount of enteric-coated particles is usually in the range of 0.1–20 grams, preferably 0.2–10 grams per dosage for horses. The total volume of the final gel given to horses is in the range of 5–50 ml.

Other suitable substances which may be incorporated in the composition are flavouring substances known in the pharmaceutical field.

The suitable substances may be added to the enteric-coated proton pump inhibitor particles by mixing the different substances with the enteric-coated particles to a mixture or an ordered mixture. An ordered mixture may be produced for example by particle adhesion or coating processes.

The mixtures of enteric-coated proton pump inhibitor particles and the suitable constituents are dried before or after mixing to a moisture level where the proton pump inhibitor has a good long-term stability. The mixture is preferably dispensed into a tight applicator preferably in the form of a syringe.

The mixture of the enteric-coated proton pump inhibitor beads or tablets and other constituents can also comprise a suitable pH-buffering substance which will improve the functional stability of the formulation during its transport through the oesophagus and stomach before it reaches the small intestine where the proton pump inhibitor is dissolved and absorbed. Suitable buffering substances are citric acid, tartaric acid, succinic acid, malic acid, lactic acid, benzoic acid, sorbic acid and ascorbic acid and other substances. Such substances will decrease the pH-value of the gel produced to a value below 5.5, thus protecting the enteric coating of the beads or tablets.

Further the mixture of the enteric coated proton pump inhibitor particles and suitable constituents may also comprise inert particles, such as inert beads to facilitate the mixing of the different constituents with the enteric-coated particles. Such inert beads are for example beads of coated sugar or any other kind of beads not harmful to the animal.

Enteric coated beads or tablets can be prepared by conventional methods. Enteric-coated pellets of omeprazole can for instance be prepared as described in the U.S. Pat. No. 4,786,505 (=EP 247983) hereby incorporated by reference in its entirety. Such enteric coated pellets or beads of omeprazole are preferably coated with at least two coatings one of which is an isolation coating/subcoat and the other is an enteric coating.

The preparation of a stable pharmaceutical composition according to the invention is performed by incorporating a proton pump inhibitor in the form of beads or tablets, which are coated with one ore more coatings one of which is an enteric-coating, into a paste-like gel.

More particular, the preparation of a formulation in the form of a paste-like gel is performed by either I) mixing the coated particles of the proton pump inhibitor with a dry gelling agent and optionally a pH-buffering system protecting the coated particles whereafter water is added ex tempore, just prior to administration to the animal, or II) mixing the coated particles with a potassium or calcium ion containing salt and optionally a pH-buffering system and thereafter ex tempore, just prior to administration to the animal, with a low-viscous water solution of a gelling agent such as a polymer compound or compounds or by III) mixing the coated particles ex tempore, just prior to administration to the animal, with a low-viscous solution of a gelling agent in the form of temperature-sensitive polymer and optionally with a pH-buffering system and then subjecting the mixture to gentle heating.

EXAMPLES

The omeprazole enteric-coated pellets in the examples below are prepared

| | Uncoated pellets | |
|---|---|---|
| I | Mannitol powder | 16 150 g |
| | Lactose anhydrous | 800 g |
| | Hydroxypropyl cellulose | 600 g |
| | Microcrystalline cellulose | 400 g |
| II | Omeprazole | 2 000 g |
| | Sodium lauryl sulphate | 50 g |
| | Disodium hydrogen phosphate | 80 g |
| | Distilled water | 4 400 g |

The dry ingredients (I) were premixed in a mixer. Addition of a granulation liquid (II) containing suspended omeprazole was made and the mass was wet-mixed to a proper consistency. The wet mass was pressed through an extruder and spheronized to pellets. The pellets were dried and classified into suitable particle size ranges.

| | Subcoated pellets | |
|---|---|---|
| II | Uncoated omeprazole pellets | 6 000 g |
| | Hydroxypropyl methylcellulose | 240 g |
| | Distilled water | 4 800 g |

The polymer solution (III) was sprayed on the uncoated pellets in a fluidized bed apparatus. The spray guns were placed above the fluidized bed.

| | Enteric-coated pellets | |
|---|---|---|
| IV | Subcoated pellets | 500 g |
| | Hydroxypropyl methylcellulose phthalate | 57 g |
| | Cetyl alcohol | 3 g |
| | Acetone | 540 g |
| | Ethanol | 231 g |

The polymer solution (IV) was sprayed on the subcoated pellets in a fluidized bed apparatus with spray guns placed above the bed. After drying to a water content of 0.5% the enteric coated pellets were classified . . .

Example 1

| | |
|---|---|
| Omeprazole enteric-coated pellets (corresponding to about 600 mg of omeprazole) | 7 g |
| Xanthan gum | 0.3 g |
| are mixed in a syringe. | |
| When 10 ml of water are added a viscous gel is formed. | |

Example 2

| | |
|---|---|
| Omeprazole enteric-coated pellets | 7 g |
| Xanthan gum | 0.3 g |
| Citric acid | 60 mg |
| are mixed in a syringe. | |
| When 10 ml of water are added a viscous gel is formed. | |

Example 3

| | |
|---|---|
| Omeprazole enteric-coated pellets | 7 g |
| Potassium chloride | 30 mg |
| are mixed in a syringe. | |
| When 10 ml of a 1% solution of kappa-carrageenan are added a viscous gel is formed. | |

Example 4

| | |
|---|---|
| Omeprazole enteric-coated pellets | 7 g |
| are dispensed into a syringe. | |
| When 10 ml of a solution of EHEC (ethylhydroxyethylcellulose) 1.25% and sodium lauryl sulphate 0.1% are added and warmed to 35° C. a viscous gel is formed. | |

Example 5

| | |
|---|---|
| Lansoprazole enteric-coated pellets (prepared according to examples 1 and 2 of EP 277 741, Example 1 | 10 g |

Nonpareils (20–28 mesh), 2250 g. were brought into the CF grandulator (CF-360, Freund Industrial Co., Ltd., Japan), and coated, while being sprayed with 2000 ml of hydroxypropylcellulose solution (3% (w/v)) at 25 ml/min. first with the spraying powder 1 and then the spraying powder 2, both of which had been prepared by mixing the ingredients listed below, at the rate of 45 g/min at room temperature with a rotor rotating at 20 rpm. dried under -continued reduced pressure at 40° C. for 16 hours, and sieved through round sieves, to give spherical granules having a core of 12–32 mesh.

Spraying powder 1

| | |
|---|---|
| compound A | 450 g |
| magnesium carbonate | 450 g |
| sucrose | 450 g |
| corn starch | 45 g |
| L-HPC | 450 g |

(degree of substitution with hydroxypropyl group: 10.0—13.0% (w/w), mean particle size: not more than 30 μm. The particles of the same degree of substitution and particle size were used hereinafter.

spraying powder 2

| | |
|---|---|
| sucrose | 420 g |
| corn starch | 360 g |
| L-HPC | 360 g |

Example 2

The granules obtained in Example 1, 3800 g. were brought into the fluidized-bed coater (Okawara Co., Japan), subjected to enteric coating by spraying the enteric coating film solution described below at the rate of 50 ml/min under the controlled conditions of inlet air at 50° C. and material temperature at 40° C., to give enteric coated spherical granules having core.

Enteric coating film solution

| | |
|---|---|
| Eudragit L30D-55 | 628 g |
| talc | 192 g |
| polyethyleneglycol 6000 | 64 g |
| titanium oxide | 64 g |
| Tween 80 | 32 g |
| water | 4400 ml | h#r#hy ;nccrpcrat#d by #
(corresponding to lansoprazole ~900 mg)

| | |
|---|---|
| Xanthan gum | 0.45 g |
| Citric acid | 80 mg |

When 15 m of water are added a viscous gel is formed.

Example 6

| | |
|---|---|
| Pantoprazole enteric-coated pellets | 7 g |

(prepared according to example 2 of EP 519 365, Pellets

I. Starter

| | |
|---|---|
| a) saccharose pellets (0.7–0.85 mm) | 950.0 g |
| b) hydroxypropylmethyl cellulose | 50.0 g | a) is sprayed with the aqeous solution of b) in a fluidized bed (Wurster method).

II. Active pellets

| | |
|---|---|
| c) pantoprazol-Na-sesquihydrate | 403.0 g |
| d) hydroxypropylmethyl cellulose | 40.3 g | c) and d) are dissolved in 30% isopropanol, one after the other, and sprayed onto 900 g of the starter pellets obtained under I., in a fluidized bed (Wurster method).

III. Pre-insulation (intermediate layer)

Coating takes place analogous to the method of procedure described for the tablets, in a vat or in a fluidized bed.

IV. Coating resistant to gastric juices

Coating takes place analogous to the method of procedure described for the tablets, in a vat or in a fluidized bed.

hcr#by incorpcratcd by ref&ence)
(corresponding to pantoprazole ~1200 mg)

| | |
|---|---|
| Xanthan gum | 0.3 g |
| Citric acid | 50 mg |

When 10 ml of water are added a viscous gel is formed.

The best mode of carrying out the invention known at present is to use the composition described in Example 2.

What is claimed is:

1. An oral pharmaceutical composition for easy administration to the tongue of a horse or other animal comprising:

(a) a dry component comprising a mixture of (i) an enteric coated particle comprising as active ingredient a therapeutically effective amount of a proton pump inhibitor or $H^+K^+$ATPase enzyme inhibitor compound selected from the group consisting of omeprazole, lansoprazole, pantoprazol, E-3810, leminoprazole, and S-4216, in neutral form or in the form of pharmaceutically acceptable salt selected from the group consisting of a $Mg^{2+}$, $Ca^{2+}$, $Na^+$ and $K^+$ salt; (ii) a gel forming agent; and (iii) a buffering agent;

(b) a wet component comprising water or a water solution of a gel forming agent; the quantities of the dry and the wet component are proportioned so as to form a gel having the cohesive consistency of a paste.

2. The composition according to claim 1, wherein the particle is a bead or a tablet or a plurality thereof.

3. The composition according to claim 1, wherein the gel forming agent (ii) is a calcium or potassium containing salt so as to cause a water solution of a gel to form a gel having the consistency of a paste.

4. The composition according to claim 2, wherein the bead or the tablet has a subcoating layer located underneath the enteric coating layer.

5. The composition according to claim 1, wherein the inhibitor compound is a racemate or an enantiomer.

6. The composition according to claim 1, wherein the component (a) is in the form of an ordered mixture.

7. The composition according to claim 1, wherein the buffering agent comprises a compound which causes a wet gel pH value to a level less than the critical pH at which the enteric coating will dissolve.

8. The composition according to claim 1, wherein the buffering agent comprises a compound which causes a wet gel pH value to a level less than about 5.5 so as to stabilize the enteric coating of the particle in the gel.

9. The composition according to claim 1, wherein the dry component (a) further comprises (iv) a flavoring agent.

10. A pharmaceutical composition according to claim 1, wherein the proton pump inhibitor is omeprazole.

11. A pharmaceutical composition according to claim 1, wherein the proton pump inhibitor is lansoprazole.

12. A pharmaceutical composition according to claim 1, wherein the proton pump inhibitor is pantoprazole.

13. A pharmaceutical composition according to claim 1, wherein the proton pump inhibitor is leminoprazole.

14. The composition according to claim 1, wherein the dry component (a) further comprises (v) a water soluble organic or inorganic salt of potassium, calcium, magnesium or aluminum.

15. The pharmaceutical composition according to claim 1 wherein the composition in its entirety or parts thereof is dispensed into an applicator being in the form of a syringe.

16. Method for treatment of gastric acid related diseases wherein a physiologically active amount of a composition according to claim 1 is administered to an animal in the need of such treatment.

17. The pharmaceutical composition according to claim 1, wherein the gel forming agent is temperature sensitive so as to form a gel having the consistency of a paste when subjected to gentle heating to about 35°.

* * * * *

UNITED STATES PATENT AND TRADEMARK OFFICE
CERTIFICATE OF CORRECTION

PATENT NO. : 5,731,002
DATED : March 24, 1998
INVENTOR(S) : Olovson et al.

It is certified that error appears in the above-indentified patent and that said Letters Patent is hereby corrected as shown below:

Claim 17 at column 8, line 61: "35°" should be -- 35°C --.

Signed and Sealed this

First Day of June, 1999

Q. TODD DICKINSON

Attest:

Attesting Officer

Acting Commissioner of Patents and Trademarks